United States Patent [19]

Dalsgard et al.

[11] Patent Number: 5,716,848
[45] Date of Patent: Feb. 10, 1998

[54] CULTURED CELLS OF QUILLAJA SP

[75] Inventors: Kristian Dalsgard, Kalvehave, Denmark; Max Henry, Toulouse, France

[73] Assignee: Seed Capital Investment (SCI) B.V., Utrecht, Netherlands

[21] Appl. No.: 424,449

[22] PCT Filed: Oct. 29, 1993

[86] PCT No.: PCT/NL93/00220

§ 371 Date: Aug. 7, 1995

§ 102(e) Date: Aug. 7, 1995

[87] PCT Pub. No.: WO90/03184

PCT Pub. Date: Apr. 5, 1990

[30] Foreign Application Priority Data

Oct. 30, 1992 [EP] European Pat. Off. ............ 92203365
Dec. 7, 1992 [NL] Netherlands ..................... 9202117

[51] Int. Cl.$^6$ .................................................. C12N 5/100
[52] U.S. Cl. ....................... 435/410; 435/420; 435/421; 435/430.1; 424/195.1; 424/193.1
[58] Field of Search .............................. 435/240.4, 410, 435/420, 421, 430.1, 240.45, 240.46, 240.48; 424/195.1, 193.1

[56] References Cited

U.S. PATENT DOCUMENTS 5,057,540 10/1991 Kensil et al. ..................... 514/25

FOREIGN PATENT DOCUMENTS

WO 92/06710 4/1992 WIPO.

OTHER PUBLICATIONS

Henry, M et al., Quillaic acid production in Saponaria officinalis cell suspension culture, *Chem Abs* 97(25):688, abstract 97:214231c 1982.

Neumüller, O.-A., Römpps Chemie–Lexikon, 8ste Ed., 1987, Franckh'sche Verlagshabdlung, Stuttgart, Germany, p. 3452 (with Translation).

Chemical Abstracts, White, et al., A purified saponin acts as an adjuvant for a T–independent antigen, 117:5649n Jul. 6, 1992.

Chemical Abstraacts, Gaunt, et al., Short term toxicity of quillaia extract in rats, 82:56161p Mar. 3, 1975.

E.F. Steinmetx, Codex Vegetablis, No. 941 1957.

*Primary Examiner*—John W. Rollins
*Attorney, Agent, or Firm*—Christensen O'Connor; Johnson & Kindness PLLC

[57] ABSTRACT

The present invention relates to cultured cells of Quillaja sp. For the preparation of active substances from Quillaja sp., such as saponins. The cells may either originate from a callus tissue culture or from a suspension cell culture. Preferred Quillaja sp. are species selected from the group consisting of *Quillaja saponaria Molina, Quillaja smegmadermos, Quillaja brasiliesis*. The invention further relates to active substances extracted from cultured cells of Quillaja sp. and to preparations comprising these active substances, or a non-dialysable or a dialysable fraction thereof, to methods for preparing the active substances and to various agents, comprising the dialyzable and/or the non-dialysable fraction of an extract of cultured cells of Quillaja sp. And having various properties.

18 Claims, 4 Drawing Sheets

Fig. 5

CULTURED CELLS OF QUILLAJA SP

This application is the national phase of PCT NL93/00220, filed Oct. 29, 1993, and claims priority under 35 U.S.C. §119, based on EP 92203365.9, filed on Oct. 30, 1992.

The present invention relates to cultured cells of Quillaja sp., a method for preparing active substances from Quillaja sp., various products comprising the active substances, a method for preparing Immune-Stimulating COMplexes (ISCOM's) from the active substances and vaccins and adjuvants comprising the ISCOM's, the adjuvant ISCOM-matrix (Lövgren, K. thesis, ISBN 91-576-3202-2), the adjuvant Quil A (Dalsgaard, K., Arch. ges. Virusforsch. 44, 243–254 (1974), the adjuvant QS 21 (Jia-Yan Wu, J. Immunology 148, 1519–1525 (1992), and other saponin adjuvants.

Immune-stimulating complexes (so-called ISCOM's) are negatively charged pentagonal dodecahedra that form spontaneously on mixing cholesterol and the saponins of Quillaja sp. During their formation proteins and other lipids can be incorporated. ISCOM's have been found to strongly enhance immune responses and are therefore used as an immunological adjuvant and carrier/delivery system in e.g. vaccines. Quil A, QS 21, and other saponin adjuvants are products derived from the natural bark having immunological adjuvant activity in a variety of vaccines.

For the production of ISCOM's there is a growing need for inter alia Quil A. Quil A is a mixture of the active substances (saponins) originating from the bark of the Quillaja sp. tree growing mainly in Chile. The natural sources of Quillaja bark are limited. In fact, old trees are already rare today and yet about 1000 tons of bark per year are exported from Chile. Because the increasing demand for active substances (sapanins) for various purposes a shortage of material is to be expected in the future.

It is therefore highly desirable to find other ways of isolating Quil A and other active substances of Quillaja (saponins) for the preparation of ISCOM's, as adjuvants, and for various other applications.

It has now been found that cells, tissues or organs of the Quillaja sp. plant body can be cultured in vitro in a liquid or on a solid medium.

The invention thus provides cultured cells of Quillaja sp. for the preparation of active substances from Quillaja sp. The cultured cells may originate from a callus cell culture, wherein tissues or organs are grown on a solid medium. The term "callus" refers to an amorphous lump of cells having lost their organ-forming capacity, and which lump is formed when a fragment of the plant body is tissue cultured on a solid medium. The so obtained callus shows an external form resembling the agglutination tissue of the plant body. The cultured cells may also originate from a suspension cell culture. The term "suspension" cell culture refers herein to a fine flocky dispersion of the cells formed when pieces of callus are further inoculated and cultured in a liquid medium under aerobic conditions.

According to the invention various kinds of Quillaja plants can be used for tissue or suspension culture, for example *Quillaja saponaria* Molina, *Quillaja smegmadermos*, *Quillaja brasiliensis* and the like.

BRIEF DESCRIPTION OF THE DRAWINGS

In FIG. 1, "A" represents the point of application of the extract to the plate, "1" and "2" represent the two major bands, and "F" indicates solvent front.

In FIG. 2, "3" and "4" indicate the two major bands.

FIG. 5 illustrates the results of testing extracts of a cell suspension culture and a callus culture for immunological adjuvant activity, as described in EXAMPLE 6.

Figure 1:
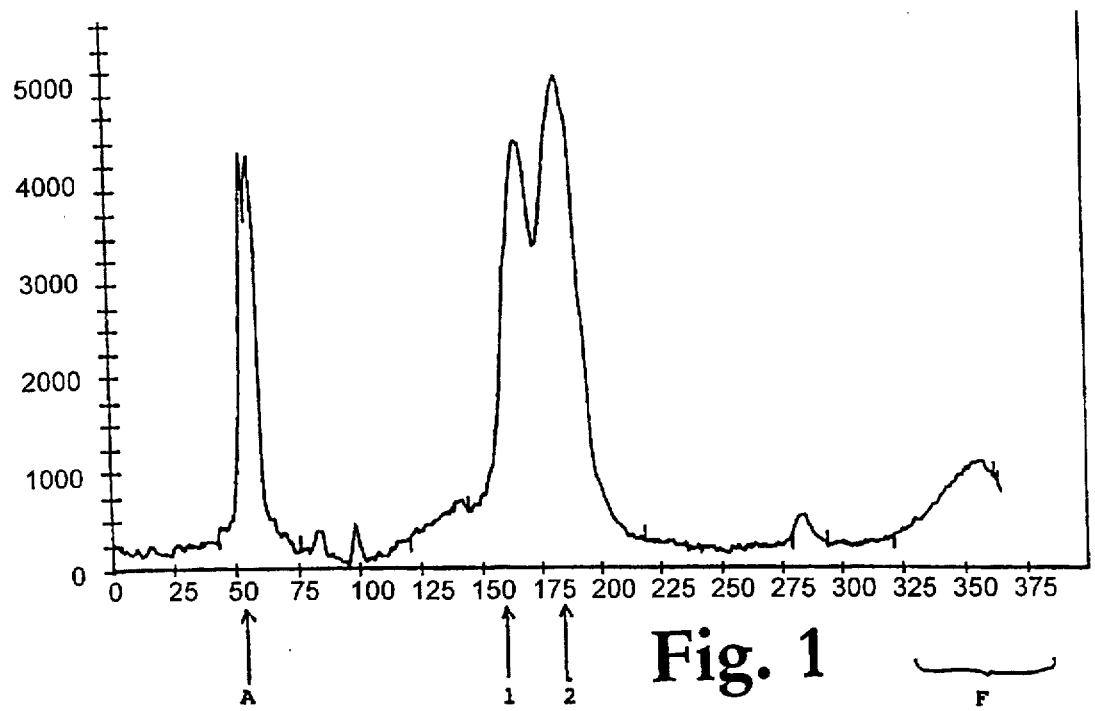
FIG. 1 shows a densitometric scan of a HPTLC plate developed as described in Example 3, to which was applied an extract from a callus cell culture.

The conventional medium-compositions for tissue cultures mentioned in the literature, for example, the media called White's medium (White P. R. Growth 7: 53 (1943)), Heller's Medium (Heller R. Thèse Sc. Nat. Paris (1953)), Murashige and Skoog's medium (Murashige T. and Skoog F. Physiol. Plant. 15: 473 (1962)), Linsmaier and Skoog's medium (Linsmaier E. M. and Skoog F. Physiol. Plant. 18, 100 (1965)), and Gamborg, Miller and Ojima's medium (Gamborg O. L., Miller R. A. and Ojima K., Exp. Cell. Res. 50, 151 (1968)), can be used in the present invention. These known media consist of inorganic substances and other trace elements which have hitherto been used in the media for the water-culture method for plants, such as saccharide, auxins (growth-promoting substance), cytokinins, vitamins and amino acids. In particular, the following are used in these media: inorganic salts selected from potassium chloride, calcium chloride, potassium nitrate, calcium nitrate, sodium nitrate, ammonium nitrate, sodium nitrate, magnesium sulfate, potassium phosphate, sodium sulfate, magnesium nitrate, ammonium nitrate, sodium sulfate, magnesium sulfate, potassium phosphate, sodium phosphate, ferric chloride, ferric sulfate, $NA_2$-EDTA ($NA_2$-ethylenediamine tetra-acetic acid), manganese sulfate, zinc sulfate, boric acid, potassium iodide, copper sulfate, sodium molybdats, aluminium chloride, cobalt chloride, and the like, saccharide selected from sucrose, glucose, fructose, mannose, and the like, auxins such as 2,4-dichlorophenoxyacetic acid, α-napthaleneacetic acid, indol-3-acetic acid, cytokinins such as kinetin, benzylaminopurine, zeatine, 2-isopentenyladenine and the like, vitamins such as thiamin hydrochloride, pyridoxin hydrochloride, nicotinic acid, myo-inositol, biotin, and amino acids such as glycin. Table 1 shows examples of conventional medium compositions for tissue-culturing.

TABLE 1

| Constituents (mg./l) | White's medium | Murashige & Skoog's medium | Linsmaier & Skoog's medium |
|---|---|---|---|
| KCl | 65 | — | — |
| $CaCl_2.2H_2O$ | — | 440 | 440 |
| $KNO_3$ | 80 | 1900 | 1900 |
| $Ca(NO_3)_2.4H_2O$ | 300 | — | — |
| $H_3BO_4$ | 1,5 | 6,2 | 6,2 |
| $MgSO_4.7H_2O$ | 720 | 370 | 370 |
| $Na_2SO_4$ | 200 | — | — |
| $NH_4NO_3$ | — | 1650 | 1650 |
| $KH_2PO_4$ | — | 170 | 170 |
| $NaH_2PO_4$ | 16,5 | — | — |
| $Fe_2(SO_4)_3$ | 2,5 | — | — |
| $FeSO_4.7H_2O$ | — | 27,8 | 27,84 |
| $Na_2EDTA$ | — | 37,34 | 37,34 |
| $MnSO_4.4H_2O$ | 7 | 22,3 | 22,3 |
| $ZnSO_4.7H_2O$ | 3 | 11,5 | 8,6 |
| KI | 0,75 | 0,83 | 0,83 |

TABLE 1-continued

| Constituents (mg./l) | White's medium | Murashige & Skoog's medium | Linsmaier & Skoog's medium |
|---|---|---|---|
| $CuSO_4.5H_2O$ | 0,0025 | 0,025 | 0,625 |
| $MoO_2$ | 0,00015 | — | — |
| $Na_2MOO_4.2H_2O$ | — | 0,25 | 0,25 |
| $COCl_2.6H_2O$ | — | 0,025 | 0,025 |
| Thiamine.HCl | 0,1 | 0,1 | 0,4 |
| Pyridoxine.HCl | 0,1 | 0,5 | — |
| Nicotinic acid | 0,5 | 0,5 | — |
| Myo-inositol | — | 100 | 100 |
| Glycine | 3,0 | 2,0 | — |
| Kinetin | — | 0,2 | 0,2 |
| Indole acetic acid | — | 2,0 | 2,0 |
| Sucrose | 20000 | 30000 | 30000 |

In order to tissue-culture Quillaja sp. according to the present invention, the plant body of Quillaja sp. plant, fragments of leaf, stem, root, flower, seed or other organs or tissues of the plant are washed, surface-sterilized, placed on the sterile agar medium for tissue-culture which is contained in a tube or flask plugged with cotton wool, cellulose or plastic cap and has one of the compositions as described in the above Table 1, and are incubated at 25°–30° C.

Said fragments or organs or tissues swell and white, yellowish-white or greenish-yellow callus is derived in 2–6 weeks. Such callus can be gradually purified by means of repeating the similar solid medium-culturing, that is, by inoculating fresh solid medium by turns with small pieces of callus formed in the previous solid medium-culturing.

The callus thus reformed and refined on the solid medium by subculture in then inoculated into a liquid medium having one of the compositions as described in Table 1, and cultured on a shaker at temperature of 25°–30° C. for 2–3 weeks in order to obtain a suspension cell culture. The inoculum is e.g. about 3 g (by fresh weight) of callus to 100 ml of liquid medium, and the callus propagates in the culture liquid in the state of a flocky suspension, that is, as "Quillaja cells". These Quillaja cells are further subcultured by repeating the similar shake-culture in liquid medium, that is, by inoculating fresh liquid medium by turns with a portion of the previous suspension cultured containing Quillaja cells.

The suspension culture obtained in the shake-culture is, after scale-up, inoculated into a liquid medium set in a bioreactor made of pyrex or stainless steel, and cultured with aeration while being agitated gently. The quantity of inoculum is one tenth of the quantity of whole medium, and intensive agitation is unfavorable because the membranes of Quillaja cells are broken thereby. The amount of air to aerate is 0.2–30 liters/liter of medium/minute and the culturing period is 2–3 weeks, i.e. the same as that of the above shake-culture. The yield of dried weight of these Quillaja cells is 30–35 percent of sugar consumed in the suspension culture and amounts to 6.9 g per liter of the medium. It will take 2–6 weeks for agar medium culture and 2–3 weeks for each liquid shake-culture and aeration-liquid bioreactor culture, totalling to 6–12 weeks, to obtain a suspension containing Quillaja cells as raw material for the preparation of active substances from which saponins for the formation of ISCOM's might be isolated. However, when the suspension culture is once obtained in the aeration-culture in the bioreactor, a semi-continuous process may be adopted, wherein one portion of the culture is taken out to leave the other portion thereof in the bioreactor and fresh sterile medium is supplemented to the remaining portion so as to carry on the culturing of Quillaja cells.

The active substances prepared from the cultured cells of Quillaja sp. are mainly saponins. Saponins are a type of glycosides widely distributed in plants. Saponins consist of a sapogenin which constitutes the aglucon moiety of the molecule, and several sugars. The sapogenin is in this case a triterpene and the sugar moiety may consist of rhamnose, fucose, arabinose, xylose, galactose, glucose, glucuronic acid, and possibly other minor sugars.

The invention further relates to a method for preparing active substances from Quillaja sp. comprising the steps of:
a) culturing cells from Quillaja sp. in vitro; and
b) preparing a cell culture extract comprising the active substances.

It has been found that the extract of Quillaja sp. cell culture comprising active substances can be separated into two fractions, one being a non-dialysable fraction and the other one being a dialysable fraction. The term "dialysable" as used herein refers to compounds removed from a dialysis sack after dialysing a crude extract of a Quillaja sp. cell culture against saline for about 24 hours. The term "non-dialysable" us used herein refers to compounds retained in a dialysis sack after dialysing a crude extract of a Quillaja sp. cell culture against saline for about 24 hours.

Both the dialysable and the non-dialysable fraction show interesting properties. The compounds of the dialysable fraction are first of all capable of inducing foam in aqueous solutions. This is demonstrated by the fact that the dialysate is foaming readily when shaken. Furthermore the active substances of the dialysable fraction can act as emulsifiers for producing oil-in-water emulsions showing similar properties as the compounds of the "Tween" series. For example, experiments showed that 9 ml of dialysate and 1 ml of mineral or biodegradable oil, such as squalane, forms a stable emulsion when shaken vigorously or treated by ultrasonification. The dialysable fractions are also capable of binding ammonia.

The dialysable fraction from the active substances obtainer from the cultured cells of Quillaja sp. therefore have properties which can be utilized for similar technical purposes as extracts of the natural bark. Examples of said technical purposes are their use as emulsifiers in food and beverages and in photographic film emulsions. They are also useful as additives in the treatment of waste water and slurries because the dialysable active fraction breaks down surface crusts and reduces ammonia- and odor formation in waste water plants, slurry tanks for liquid manure in pig production stables, slurry containers and the like, thus facilitating microbial and/or enzymatic breakdown and reducing odor of industrial-, household-, farm- and animal waste. They may also be used as an additive to animal feeds to reduce odor of their excrements, and to increase the utilization of feed. Their foaming ability renders them useful as additives in beverages, such as soft drinks, or as a foam producing agent in fire extinguishers. They may also be used as detergents in e.g. shampoos and the like.

The non-dialysable and possibly some of the dialysable fraction contains the active substances that are useful as ISCOM-forming and adjuvant agents. The substances are non-dialysable because they have a strong intrinsic characteristic of forming micelles. These micelles have the capacity to complex with cholesterol and other lipids leading to ISCOM formation. But these properties also means that the retained substances are hemolytic to red blood cells such as SRBC (sheep red blood cells). This hemolytic property can be used for their assay in the cell culture extracts.

The matrix of immune-stimulating complexes of the invention is preferably constructed by:

a) preparing a non-dialysable fraction from an extract of cultured cells of Quillaja sp.;
b) adding at least one lipid and at least one detergent to the non-dialysable fraction;
c) allowing the ISCOM's or ISCOM-matrix to form; and
d) removing the detergent.

The ISCOM's thus prepared are very well suited to be used in various vaccins as immunological adjuvants.

The cultured cells of the present invention are advantageous in many respects for preparing active substances of Quillaja sp.

For example, the natural source for the immunological and ISCOM-forming substances is a highly variable material, the individual components of which are difficult to separate. The cultured cells of the invention are a much more reliable way of producing the active substances. Another advantage is that the culture cell extracts can be validated under good manufacturing principles. The cultured cell products are free from many of the e.g. coloured substance in the natural extract from the plant. The resulting product is much more homogeneous.

The cell cultures, especially the suspension cultures, can be subcloned to establish cell lines which will produce individual substances rather than a group of related substances, which is the case in the natural plant. In the examples it will be demonstrated that one of the obtained suspension culture cells produce a much more restricted saponine pattern in HPTLC than the callus culture from which it is derived, which itself is already more restricted than natural extracts.

The cultured cells for preparing active substances will be cheaper when scaled up because the fermentation of plant suspension cell culture is straight forward and the medium is inexpensive in large volumes. Furthermore the active substances will be much easier to purify and validate than substances from the natural plant, because all parameters governing the production and purification can be monitered in a reliable way.

The present invention will be further illustrated by means of the following examples that are in no way intended to limit the scope of the invention.

EXAMPLE 1

Preparation of cultured cells

The internode explants of stems of *Quillaja saponaria* Molina where surface sterilised with first aqueous ethanol 70° B (1 min.) and NaOCl 20° Ch with a drop of Teepol per liter for 20 minutes (exactly twice 10 min.), rinsed 3 times with sterile distilled water and put on a solid modified Murashige and Skoog's basal medium (M. and S. Physiol. Plant. 1962 15, 473) usually used for plant cell cultures. The modifications concern carbohydrates: saccharose is replaced by glucose (same concentration), KCl: 0.75 mg/l instead of 0.83, vitamins: thiamine. HCl 1 mg/l, nicotinic acid 0.1 mg/l, pyridoxin. HCl 0.1 without glycin and pH 5.7. This medium was previously used with success for tissue culturing *Saponaria officinalis* and *Gypsophilla paniculata*. To this basal medium were added two phytohormones: one auxin selected from 2,4 D (2,4-dichlorophenoxyacetic), NAA (naphtaleneacetic acid) or IBA (indolbutyric acid) in three concentrations: $10^{-5}M$, $10^{-6}M$ or $10^{-7}M$; and one cytokinin selected from kinetine (K) or benzylaminopurine (BAP or BA). Then 54 mediums were prepared and 5 explants were put on each type of medium in test-tubes of 25 cm length and 2.5 cm width (diameter). These tubes were put in a culture room at 25° C. and a 12 hour photoperiod of classical white neons.

After 3 to 6 weeks primary calluses appeared and were subcultured on the same fresh medium. The callus cultures obtained on each medium are considered as one original cell line. The frequency of the subculture of each cell line depended upon the growth rate of the cell and varied from one month to three months. The cell lines not subcultured after three months (the growth rate being too slow) were discarded. Six months after obtention of the callus lines (the shortest time necessary to consider the cell line as stable as possible) callus biomass of the main cell lines were tested to estimate the saponin content and first cell suspension were established from each callus cell line to improve the growth rate and then the biomass production. One of the suspension cell lines, named NAA $10^{-5}M/K 10^{-6}M$, was detected to be an ISCOM saponin producing cell line.

Some of the choices in these conditions of obtention of these cell lines are the fruit of own experience of the inventors. For example, internodes are used directly instead of other parts of the stem (nodes and sleaves) because it was found by Japanese scientists in using *Panax ginseng* (Kubo et al, J. Nat. Prod. 1980, 43, 278) and in using *Bupleurum falcatum* (Tani et al, J. Chromatogr. 1986, 360, 407) and by the inventors in using *Gypsophila paniculata* (Henry et al, Phytochemistry 1991, 30, 1819) that the saponin biosynthesis occurred in the phloem part of the stem in the plants that were studied. It is therefore considered the best to put the biosynthetic part of the plant in culture to obtain the production of the compound in vitro. It seems to be evident but it is not shared by many persons skilled in the art because it is thought that the plant cells could become totipotent in vitro. Theoretically each cell of each part of a plant producing one secondary compound would be able to proliferate while keeping its biosynthetic property, but until now this has not been possible for a number of plant species, because the very precise molecular biological mechanisms bringing about the cell proliferation in plants are as yet poorly understood. It is possible that one of the definite tissues in the plant able to proliferate to give cell cultures seems to be the cambium. On the other hand the cambium might be the tissue that gives rise to the phloem tissue in the whole plant and in vitro cultures.

EXAMPLE 2

Extraction Procedure

To avoid any possible breakdown of substances, both callus and suspension cell culture solids were lyophilized after harvesting. The lyophilized solids were kept in the freezer at −20° C. until use.

To make an extract these solids were weighed out and 10 times as much as water was added. This suspension was homogenized firstly by "Ultraturrax" and subsequently by ultrasonic disintegration (MSE) 3×30 min. at maximum power. After stirring for 30 min. at room temperature the mixture was centrifuged at 5000 g for 30 min. The supernatant was isolated and stored at −20° C. until further analysis.

EXAMPLE 3

HPTLC 0.4 microliter of callus extracts of the cell lines was applied as a band by use of a Deaga applicator to HPTLC plates, Merck Kieselgel 60 10×10 cm. The plates were developed in a Camag horizontal developing chamber by the solvent 200 mg $CaCl_2.2 H_2O$ dissolved in 10 ml water+40 ml methanol+40 ml chloroform.

The plates were left to saturate with vapour from 10 ml of solvents in the central chamber for 3 minutes after which the plates were developed for 25 min. by 2 ml of solvent in the reservoir. The plates were dried in a fume hood for 5 min., sprayed by a mixture of concentrated sulphuric acid in methanol 1:1, and heated in an oven for 10 min. at 120° C. The separated bands were recorded densitometrically using a 256 grey scale scanner and the Apple Macintosh software ScanAnalysis.

Almost all callus and suspension culture extracts showed the presence of two major bands. These bands correspond in their migration rate to similar bands present in extracts of the natural bark of Quillaja sp. imported from South-America. Similar to the natural compounds these two bands pass a dialysis membrane and/or ultrafiltration membranes with cut off levels higher than 10000, indicating that they do not form micelies. FIG. 1 shows the results for one of the callus cell cultures ("Lc"). "A" represents point of application, "1" and "2" represent the two major bands found in the HPTLC and "F" stands for front of the solvent.

Figure 2:
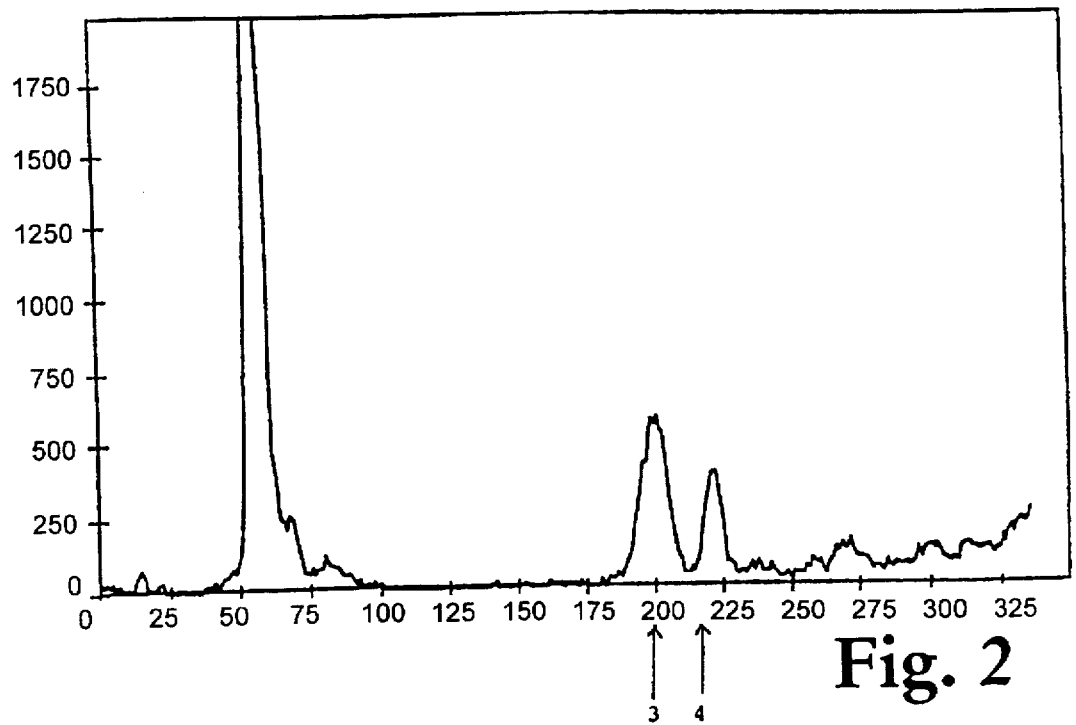
FIG. 2 shows a densitometric scan of a HPTLC plate developed as described in EXAMPLE 3, to which was applied the non-dialysable fraction of a callus cell culture extract.

After dialysis against 1 liter of saline for 24 hours the non-dialysable fraction retained in the dialysis sack is subjected to HPTLC. The results are shown in FIG. 2. "3" and "4" represent the two major bands found in the HPTLC.

EXAMPLE 4

Hemolytic Assay

Serial two-fold dilutions of plant cell culture extracts are made in 0.85% NaCl. To 1.5 ml of these dilutions are added 0.5 ml of a sheep red blood cell suspension (washed and standardized to an O.D. value of 28 at 510 nm). After end over end mixing for 10 minutes the samples are centrifuged at 2000×G for 5 minutes. The supernatants are measured spectrophotometrically at 510 nm, and the values are used as a measure for hemolysis (hemoglobin release).

Figure 4:
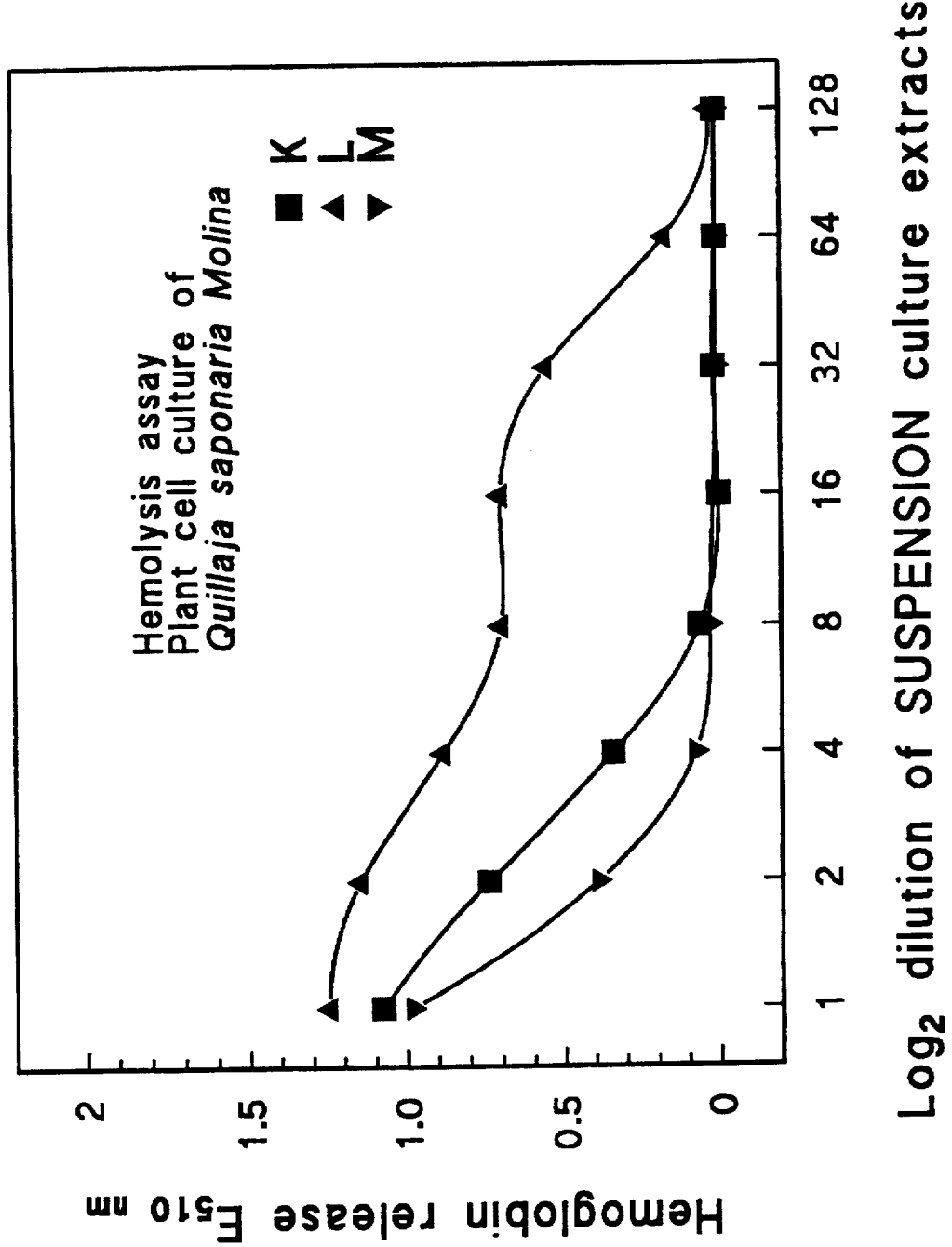
FIG. 4 graphically illustrates the hemolysis of sheep red blood cells by extracts of the various cell cultures described in EXAMPLE 4.

The results are shown in FIG. 4. The positive suspension culture extract "L" herein also called "Ls" shows a substantially higher hemoglobin release than the low-producer suspension cell culture extract "K" and than the non-producer suspension cell culture "M" herein also called "Ms".

21 extracts of callus cultures (A' to P Table 2) grown at different conditions have been tested in the same assay and show varying content of hemolytic substances: higher the longer the dashed line at the respective letter. The callus culture L in Table 2 is the basis of suspension culture L herein also called "Ls".

TABLE 2

Hemolysis index
Callus culture extracts
*Quillaia saponaria* Molina

If making arbitrary interpolations in the hemolysis curves using an absorbance at 0.5 as end point, the following values are obtained:

| | |
|---|---|
| A' | 2.5--- |
| B' | 1.2- |
| C' | 24-------------------- |
| D' | 1.9-- |
| E' | 1.4- |
| E" | 1.4- |
| F | 7.5------ |
| F' | 8.5------ |
| F" | 3.8---- |

TABLE 2-continued

Hemolysis index
Callus culture extracts
*Quillaia saponaria* Molina

If making arbitrary interpolations in the hemolysis curves using an absorbance at 0.5 as end point, the following values are obtained:

| | |
|---|---|
| F'" | 4.5----- |
| G | 9.0-------- |
| I | 2.4-- |
| J | 5.0--- |
| K | 50------------------------------------ |
| L | 20----------------- |
| M | 7.0------ |
| N | 7.0------ |
| O | 20------------------- |
| O' | 40------------------------------ |
| P | 3.4--- |

EXAMPLE 5

ISCOM Forming Capacity

Figure 3:
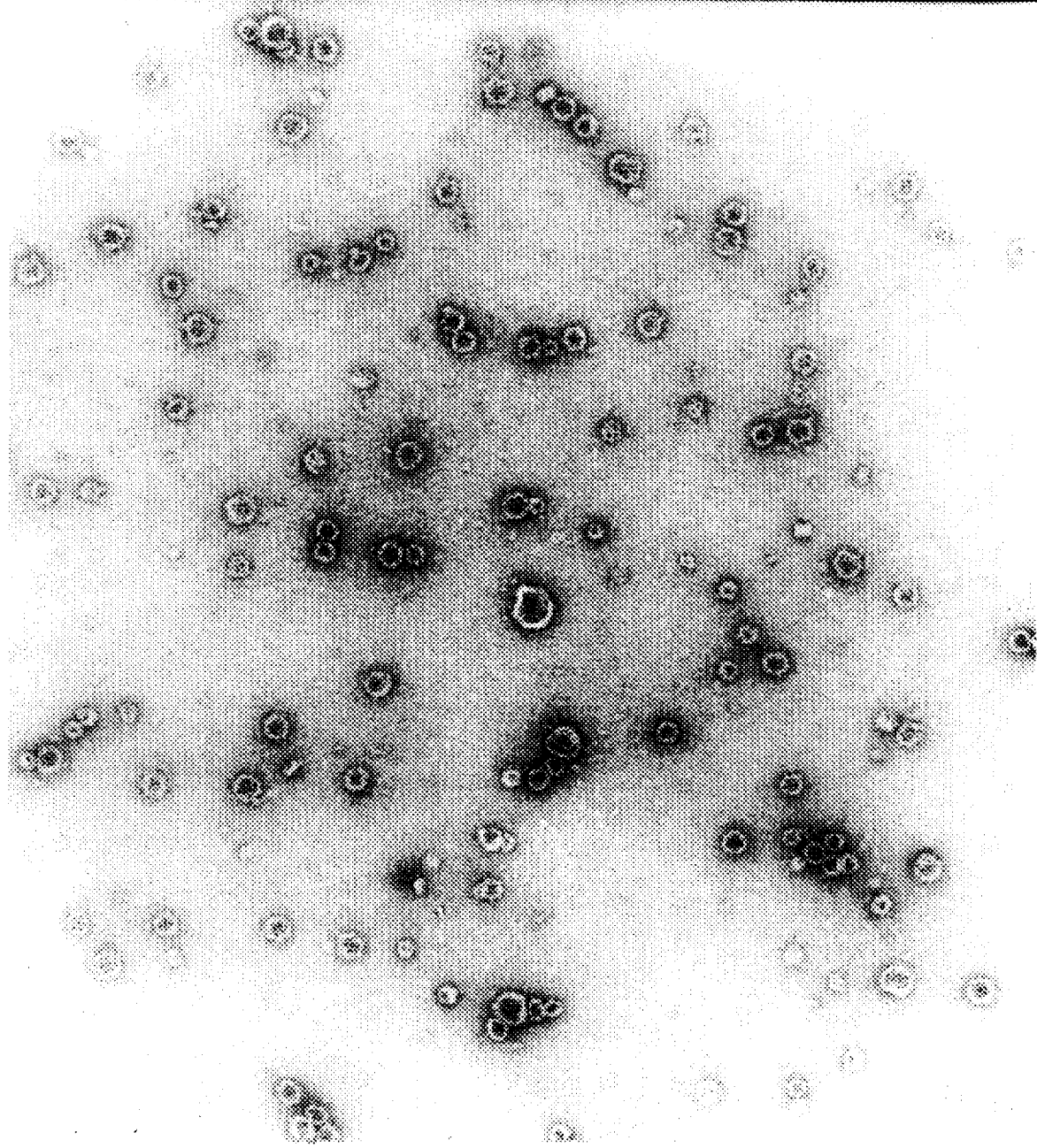
FIG. 3 shows an electron microscope photograph of the ISCOM matrices described in EXAMPLE 5.

One ml of extract "Ls" (suspension cell culture L) is dialysed against 1 liter of saline for 24 hours. To the non-dialysable fraction of the extract 10 microliters of lipid mix are added (cholesterol and phosphatidylcholine each in a concentration of 20 mg/ml in a 20% aqueous solution of the detergent MEGA 10). The mixture is turned end over end for a minimum of 1 hour to let the reaction take place. It is then dialysed again against 1 liter of saline to remove the detergent. The content of the dialysis sack is now inspected for ISCOM matrix structures in the electron microscope (EM) by negative staining with 2% uranyl acetate on carbon coated grids. FIG. 3 shows an EM photograph showing that ISCOM's have been formed.

EXAMPLE 6

Adjuvant Assay in Guinea Pigs

From the densitometric analysis of the HPTLC plates of the non-dialysable fraction of the extracts it was estimated that the loyphilized callus culture "Lc" contained about 1% of hemolytic/ISCOM matrix forming substances. The lyophilized suspension cell culture "Ls" contained about 0.5%. The "Lc" suspension cell culture was produced from the "Lc" callus culture, and since both contained substantial amounts (about the same as in the natural bark) of hemolytic and ISCOM forming saponins, the extracts of these two forms of cultures were tested for immunological adjuvant activity. A suspension cell culture extract "Ms" not producing these substances was included as a negative control. The adjuvant Quil A, extracted from the natural bark served as a positive control.

A total of 30 guinea pigs have been used for each substance tested. Three independent experiments have been made with ovalbumin as antigen, and 3 independent experiments with inactivated porcine parvovirus (PPV) as antigen. 5 guinea pigs were included in each individual group. Five groups have been tested all with antigen either ovalbumin or PPV.

Group 1: Saline control
Group 2: +Quil A, 50 micrograms, positive control.
Group 3: +callus extract "Lc", 50 micrograms.
Group 4: +suspension extract "Ls", 50 micrograms.
Group 5: +suspension extract "Ms", 50 micrograms, negative control.

Figure 5:
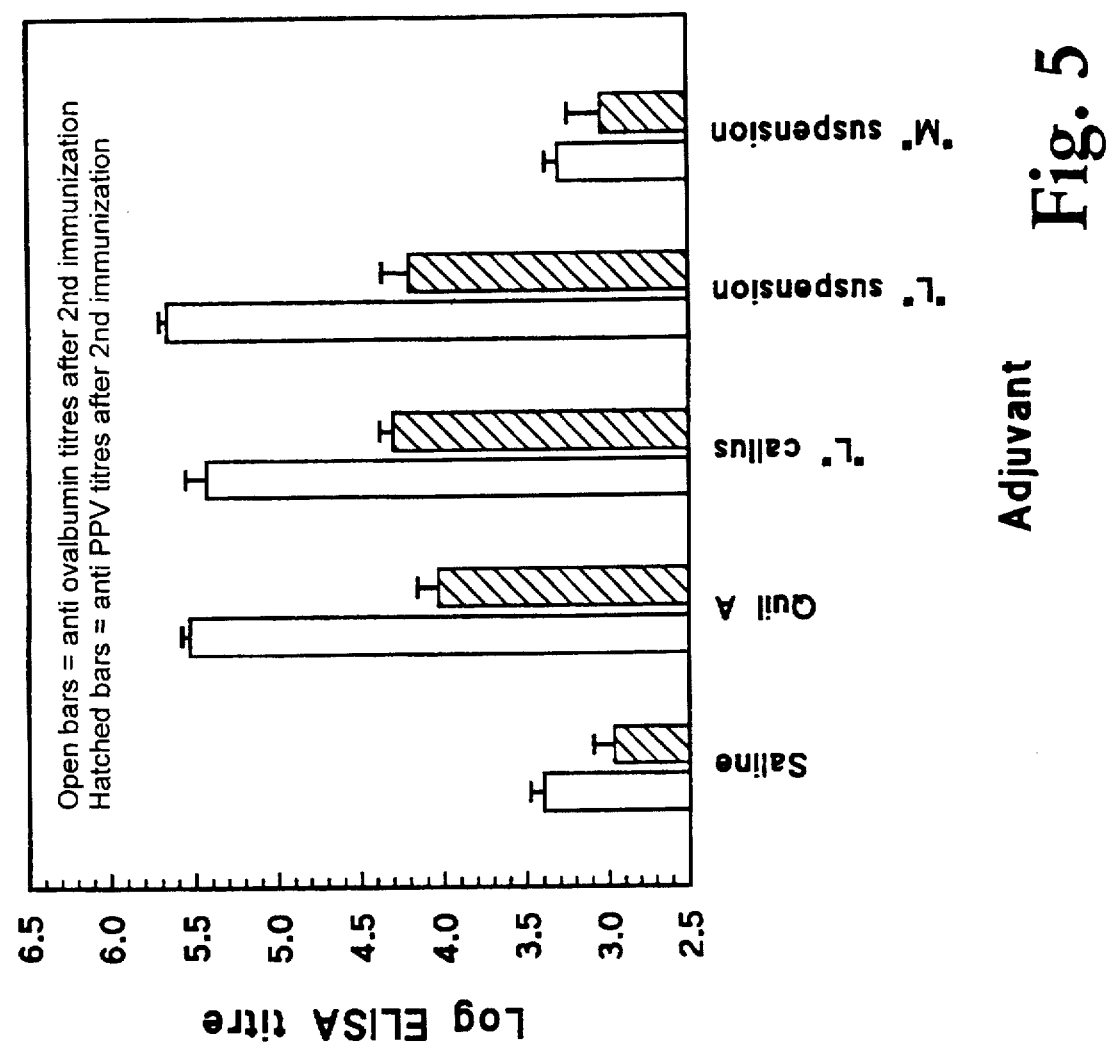

The results are shown in the FIG. 5. Both extracts "Lc" and "Ls" irrespective of whether obtained from callus or suspension plant cell culture (after dialysis) had the same adjuvant activity in guinea pigs as Quil A from the natural plant. The extract "Mc" negative for hemolytic saponins was also negative for adjuvant activity.

The present invention provides cultured cells of Quillaja sp. and a method for preparing active substances therefrom, which active substances may be used for various purposes such as ISCOM formation and as emulsifiers, detergents, foaming agents and the like.

What is claimed is:

1. A cell culture comprising cells of Quillaja sp.
2. A cell culture as claimed in claim 1, wherein the cell culture comprises a callus tissue culture.
3. A cell culture as claimed in claim 1, wherein the cell culture comprises a suspension cell culture.
4. A cell culture as claimed in claim 1, wherein the cells of Quillaja sp. are cells of a species selected from the group consisting of *Quillaja saponaria Molina, Quillaja smegmadermos*, and *Quillaja brasiliensis*.
5. A supernatant extract of cultured cells of Quillaja sp. obtained by culturing cells of Quillaja sp., forming a suspension of the cells in water, homogenizing the suspension, separating the solids from the suspension, and then recovering the supernatant.
6. A non-dialyzable fraction of an extract of cultured cells of Quillaja sp. obtainable by dialyzing a cell extract as claimed in claim 5 in a dialysis sack that does not permit passage of molecules having a molecular weight greater than 10,000 daltons against saline for about 24 hours and collecting the compounds inside the dialysis sack.
7. A method for enhancing an immune response, comprising administering an antigen and an extract of cultured cells of Quillaja sp. as claimed in claim 6.
8. A dialyzable fraction of a cell extract of cultured cells of Quillaja sp. obtainable by dialyzing a cell extract as claimed in claim 5 in a dialysis sack that does not permit passage of molecules having a molecular weight greater than 10,000 daltons against saline for about 24 hours and collecting the compounds outside the dialysis sack.
9. A method for enhancing an immune response, comprising administering an antigen and an extract of cultured cells of Quillaja sp. as claimed in claim 8.
10. A method of inducing foam in an aqueous solution comprising adding to the solution an amount effective to induce foam of an extract of cultured cells of Quillaja sp. as claimed in claim 5.
11. A method of emulsifying an aqueous solution comprising adding to the solution an amount effective for emulsification of an extract of cultured cells of Quillaja sp. as claimed in claim 5, and then mixing the solution and extract.
12. A method of binding ammonia in an ammonia-containing substance comprising adding to the substance an amount effective for binding ammonia of an extract of cultured cells of Quillaja sp. as claimed in claim 5.
13. An Immune-Stimulating Complex (ISCOM) comprising an extract of cultured cells of Quillaja sp. as claimed in claim 5, sufficient amounts of cholesterol for ISCOMs to form, and an antigen.
14. An Immune-Stimulating Complex Matrix comprising an extract of cultured cells of Quillaja sp. as claimed in claim 5, and sufficient amounts of cholesterol for ISCOM-matrices to form.
15. A method for enhancing an immune response, comprising administering an antigen and an extract of cultured cells of Quillaja sp. as claimed in claim 5.
16. A method for preparing a supernatant extract from Quillaja sp. comprising the steps of:
   a) culturing cells from Quillaja sp. in vitro; and
   b) forming a suspension of the cells in water, homogenizing the suspension, separating the solids from the suspension, and then recovering the supernatant.
17. A method as claimed in claim 16, wherein the supernatant extract is dialyzed in a dialysis sack that does not permit passage of molecules having a molecular weight greater than 10,000 daltons against saline to obtain a dialyzable and a non-dialyzable fraction.
18. A method for preparing Immune-Stimulating COMplexes (ISCOMs) or Immune-Stimulating COMplexes-matrix comprising the steps of:
   a) preparing an extract of cultured cells of Quillaja sp. by the method of claim 16 or a non-dialyzable fraction thereof by the method of claim 17;
   b) adding at least one lipid and at least one detergent to the non-dialyzable fraction;
   c) allowing the ISCOMs or Immune-Stimulating COMplexes-matrix to form; and
   d) removing the detergent.

* * * * *